US008330951B2

(12) United States Patent
Li et al.

(10) Patent No.: US 8,330,951 B2
(45) Date of Patent: Dec. 11, 2012

(54) NANO-ENHANCED RAMAN SPECTROSCOPY SUBSTRATE PACKAGING STRUCTURE

(75) Inventors: Zhiyong Li, Palo Alto, CA (US); William M. Tong, Palo Alto, CA (US); R. Stanley Williams, Palo Alto, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 1255 days.

(21) Appl. No.: 11/413,516

(22) Filed: Apr. 28, 2006

(65) Prior Publication Data
US 2007/0254377 A1 Nov. 1, 2007

(51) Int. Cl.
G01J 3/44 (2006.01)
G01N 33/00 (2006.01)
G01N 21/62 (2006.01)
H01J 9/12 (2006.01)

(52) U.S. Cl. ...... 356/301; 422/73; 422/82.05; 428/66.6; 428/343; 436/165; 436/171; 436/514; 445/51

(58) Field of Classification Search .................. None
See application file for complete search history.

(56) References Cited

U.S. PATENT DOCUMENTS

| | | | | |
|---|---|---|---|---|
| 3,779,779 | A * | 12/1973 | Landsman | 430/271.1 |
| 5,413,810 | A * | 5/1995 | Mastalski | 427/171 |
| 6,149,868 | A | 11/2000 | Natan et al. | |
| 6,699,724 | B1 | 3/2004 | West et al. | |
| 6,861,263 | B2 | 3/2005 | Natan | |
| 6,884,628 | B2 | 4/2005 | Hubbell et al. | |
| 7,384,792 | B1 * | 6/2008 | Wang et al. | 436/165 |
| 2002/0105073 | A1 * | 8/2002 | Smith | 257/730 |
| 2002/0151041 | A1 | 10/2002 | Kreimer et al. | |
| 2005/0106475 | A1 | 5/2005 | Schroeder et al. | |

OTHER PUBLICATIONS

Litorja, Maritoni, et al., "Surface-Enhanced Raman Scattering Detected Temperature Programmed Desorption: Optical Properties, Nanostructure, and Stability of Silver Film over SiO2 Nanosphere Surfaces," J. Phys. Chem. B, pp. A-I, Rec'd in Final Form May 2, 2001.
Michaels, Amy M., et al., "Surface Enhanced Raman Spectroscopy of Individual Rhodamine 6G Molecules on Large Ag Nanocrystals," J. Am. Chem. Soc., vol. 121, No. 43, pp. 9932-9939, 1999.
Premasiri, W.R., et al., "Determination of cyanide in waste water by low-resolution surface enhanced Raman spectroscopy on sol-gel substrates," J. Raman Spectrosc., vol. 32, pp. 919-922, 2001.
Voskerician, Gabriela, et al., "Biocompatibility and biofouling of MEMS drug delivery devices," Biomaterials, vol. 24, pp. 1959-1967, 2003.
UK SERS Forum, National Physical Laboratory, 11 pages, May 20, 2003.

* cited by examiner

Primary Examiner — Krishnan S Menon
Assistant Examiner — Dirk Bass

(57) ABSTRACT

Packaged NERS-active structures are disclosed that include a NERS substrate having a NERS-active structure thereon, and a packaging substrate over the NERS substrate having an opening therethrough, the opening in alignment with the NERS-active structure. A membrane may cover the opening in the packaging substrate. In order to perform nanoenhanced Raman spectroscopy, the membrane may be removed, and an analyte placed on the NERS substrate adjacent the NERS-active structure. The membrane may be replaced with another membrane after the analyte has been placed on the substrate. The membrane may maintain the pristine state of the substrate before it is deployed, and the replacement membrane may preserve the substrate and analyte for archival purposes. Also disclosed are methods for performing NERS with packaged NERS-active structures.

16 Claims, 4 Drawing Sheets

NANO-ENHANCED RAMAN SPECTROSCOPY SUBSTRATE PACKAGING STRUCTURE

FIELD OF THE INVENTION

The invention relates to nanoenhanced Raman scattering (NERS). More particularly, the invention relates to packaging for NERS-active structures, protection for surfaces of NERS-active structures, also including methods for forming packaging for NERS-active structures, and methods for packaging NERS-active structures.

BACKGROUND OF THE INVENTION

Raman spectroscopy is a well-known technique for performing chemical analysis. In conventional Raman spectroscopy, high intensity monochromatic light provided by a light source, such as a laser, is directed onto an analyte (or sample) that is to be chemically analyzed. A majority of the incident photons are elastically scattered by the analyte molecule. In other words, the scattered photons have the same energy, and thus the same frequency, as the photons that were incident on the analyte. However, a small fraction of the photons (i.e., about 1 in $10^7$ photons) are inelastically scattered by the analyte molecules. These inelastically scattered photons have a different frequency than the incident photons. This inelastic scattering of photons is termed the "Raman effect." The inelastically scattered photons may have frequencies greater than or, more typically, less than the frequency of the incident photons.

When an incident photon collides with a molecule, energy may be transferred from the photon to the molecule or from the molecule to the photon. When energy is transferred from the photon to the molecule, the scattered photon will emerge from the sample having a lower energy and a corresponding lower frequency. These lower-energy Raman scattered photons are commonly referred to in Raman spectroscopy as the "Stokes radiation." A small fraction of the analyte molecules are already in an energetically excited state. When an incident photon collides with an excited molecule, energy may be transferred from the molecule to the photon, which will emerge from the sample having a higher energy and a corresponding higher frequency. These higher-energy Raman scattered photons are commonly referred to in Raman spectroscopy as the "anti-Stokes radiation."

The Stokes and the anti-Stokes radiation is detected by a detector, such as a photomultiplier or a wavelength-dispersive spectrometer, which coverts the energy of the impinging photons into an electrical signal. The characteristics of the electrical signal are at least partially a function of the energy (or wavelength, frequency, wave number, etc.) of the impinging photons and the number of the impinging photons (intensity). The electrical signal generated by the detector can be used to produce a spectral graph of intensity as a function of frequency for the detected Raman signal (i.e., the Stokes and anti-Stokes radiation). A unique Raman spectrum corresponding to the particular analyte may be obtained by plotting the intensity of the inelastically scattered Raman photons against the frequency thereof. This unique Raman spectrum may be used for many purposes such as identifying an analyte, identifying chemical states or bonding of atoms and molecules in the analyte, and determining physical and chemical properties of the analyte. Raman spectroscopy may be used to analyze a single molecular species or mixtures of different molecular species. Furthermore, Raman spectroscopy may be performed on a number of different types of molecular configurations, such as organic and inorganic molecules in either crystalline or amorphous states.

Molecular Raman scattering of photons is a weak process. As a result, powerful, costly laser sources typically are used to generate high intensity excitation radiation to increase the otherwise weak Raman signal for detection. Nanoenhanced Raman scattering (NERS) is a technique that allows for generation of a stronger Raman signal from an analyte relative to conventional Raman spectroscopy. In NERS, the analyte molecules are adsorbed onto, or placed adjacent to, an active metal surface or structure (an "NERS-active structure"). The interactions between the molecules and the active structure cause an increase in the strength of the Raman signal. The mechanism of Raman signal enhancement exhibited in NERS is not completely understood. Two main theories of enhancement mechanisms have been presented in the literature: electromagnetic enhancement and chemical (or "first layer") enhancement. (For further discussion of these surface enhancement mechanism theories, see A. M. Michaels, M. Nirmal, & L. E. Brus, "Surface Enhanced Raman Spectroscopy of Individual Rhodamine 6G Molecules on Large Ag Nanocrystals," *J. Am. Chem. Soc.* 121, 9932-39 (1999)).

Several NERS-active structures have been employed in NERS techniques, including activated electrodes in electrolytic cells, activated metal colloid solutions, and activated metal substrates such as a roughened metal surface or metal "islands" formed on a substrate. For example, it has been shown that adsorbing analyte molecules onto or near a specially roughened metal surface made from gold or silver may enhance the effective Raman scattering intensity by factors of between 103 and 106 when averaged over the illuminated area of the sample.

The NERS substrate may be easily contaminated. Maintaining the pristine state of the substrate before it is deployed may be difficult. One solution is a disposable NERS substrate; however, this may be expensive. Additionally, it may be desirable to preserve a NERS substrate for archival purposes, such that analyte molecules may be retested. This may be useful, for example, to serve as evidence of the presence of materials used in a weapon.

Accordingly, there is a need for a protection method for NERS-active structures, both before and after use. Packaging may provide the needed protection. Thus, there is a need for packaging for NERS-active structures, methods for forming packaging for NERS-active structures, and methods for packaging NERS-active structures.

BRIEF SUMMARY OF THE INVENTION

A packaged NERS-active structure is disclosed that includes a substrate, at least one NERS-active structure disposed on the substrate, a packaging substrate having at least one opening therethrough disposed on the substrate, the opening being aligned with the NERS-active structure, and a removable membrane covering the opening.

A method of packaging a NERS active structure is disclosed that includes providing at least one NERS active structure on a first substrate, attaching a second substrate having an opening therethrough on the first substrate, the opening providing access to the NERS active structure, and providing a membrane covering the opening in the second substrate.

A method of preserving an analyte on a NERS substrate for archiving is disclosed that includes providing a packaged NERS-active structure comprising: a substrate; at least one NERS-active structure disposed on the substrate; a packaging substrate having at least one opening therethrough disposed on the substrate, the opening being aligned with the NERS-active structure; and a membrane covering the opening. The membrane covering the opening may be removed, an analyte molecule may be placed adjacent the at least one NERS-active structure, and the opening may be covered.

A method for forming a packaged NERS-active structure is disclosed that includes providing a substrate having a surface, affixing at least one NERS-active structure on the surface of the substrate, adhering a packaging substrate to the surface of the substrate, the packaging substrate having at least one opening therethrough, the at least one opening proving access to the NERS-active structure, and covering the at least one opening with a removable membrane.

The features, advantages, and alternative aspects of the present invention will be apparent to those skilled in the art from a consideration of the following detailed description taken in combination with the accompanying drawings.

BRIEF DESCRIPTION OF THE SEVERAL VIEWS OF THE DRAWINGS

While the specification concludes with claims particularly pointing out and distinctly claiming that which is regarded as the present invention, the advantages of this invention can be more readily ascertained from the following description of the invention when read in conjunction with the accompanying drawings in which:

DETAILED DESCRIPTION OF THE INVENTION

The present invention, in a number of embodiments, includes packaging for NERS-active structures, protection for surfaces of NERS-active structures, methods for forming packaging for NERS-active structures, and methods for packaging NERS-active structures.

The term "NERS-active structure" as used herein means a structure that is capable of increasing the number of Raman-scattered photons that are scattered by a molecule when the molecule is located adjacent to the structure, and the molecule and structure are subjected to electromagnetic radiation.

The term "NERS-active material" as used herein means a material that, when formed into appropriate geometries or configurations, is capable of increasing the number of Raman-scattered photons that are scattered by a molecule when the molecule is located adjacent the material, and the molecule and material are subjected to electromagnetic radiation. NERS-active materials can be used to form a NERS-active structure.

The term "analyte molecule" as used herein means a molecule upon which it is desired to perform NERS.

It should be understood that the illustrations presented herein are not meant to be actual views of any particular NERS-active structure, but are merely idealized representations which are employed to describe the present invention. Additionally, for ease of discussion, elements common to FIGS. 1 through 3 retain the same numerical designation.

Figure 1A:
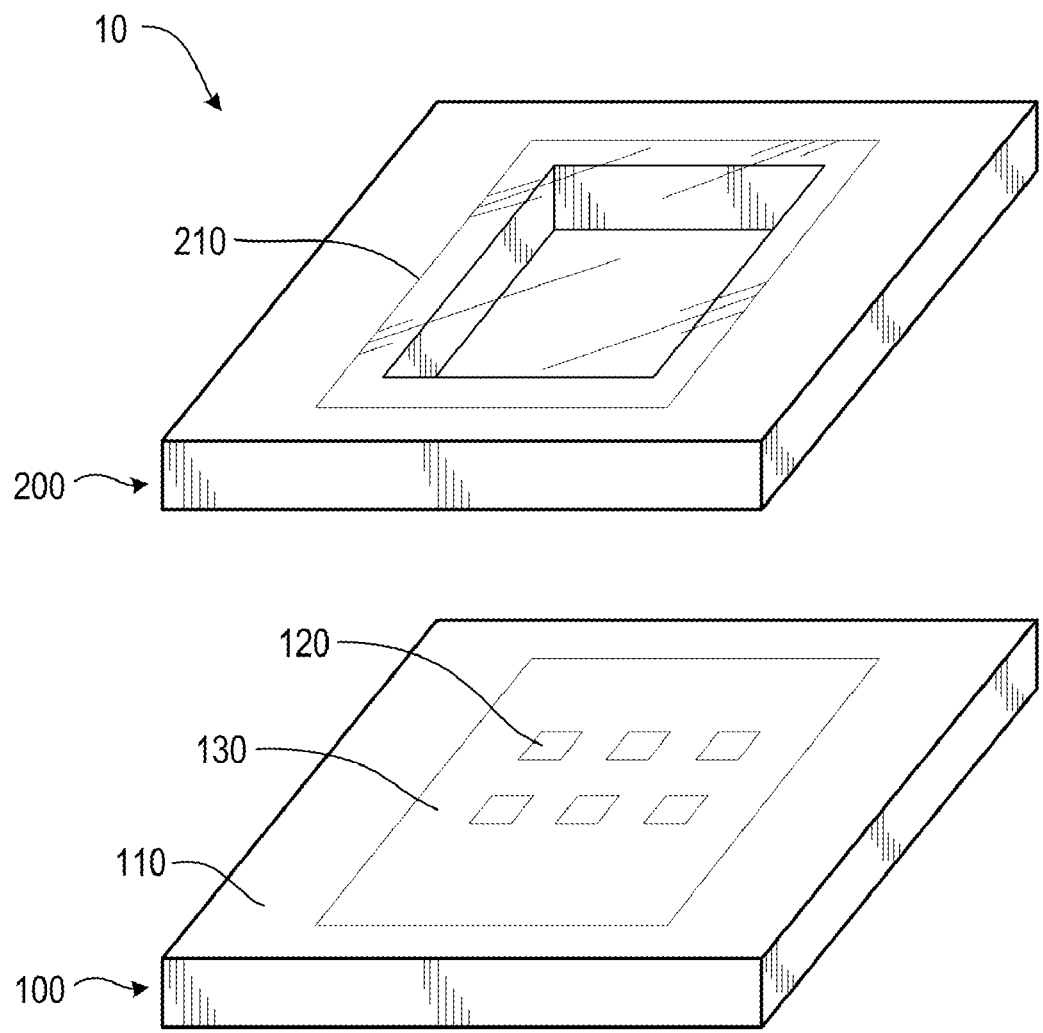
FIG. 1A is an exploded view of a first embodiment of a packaged NERS-active structure according to the invention.
Figure 1B:
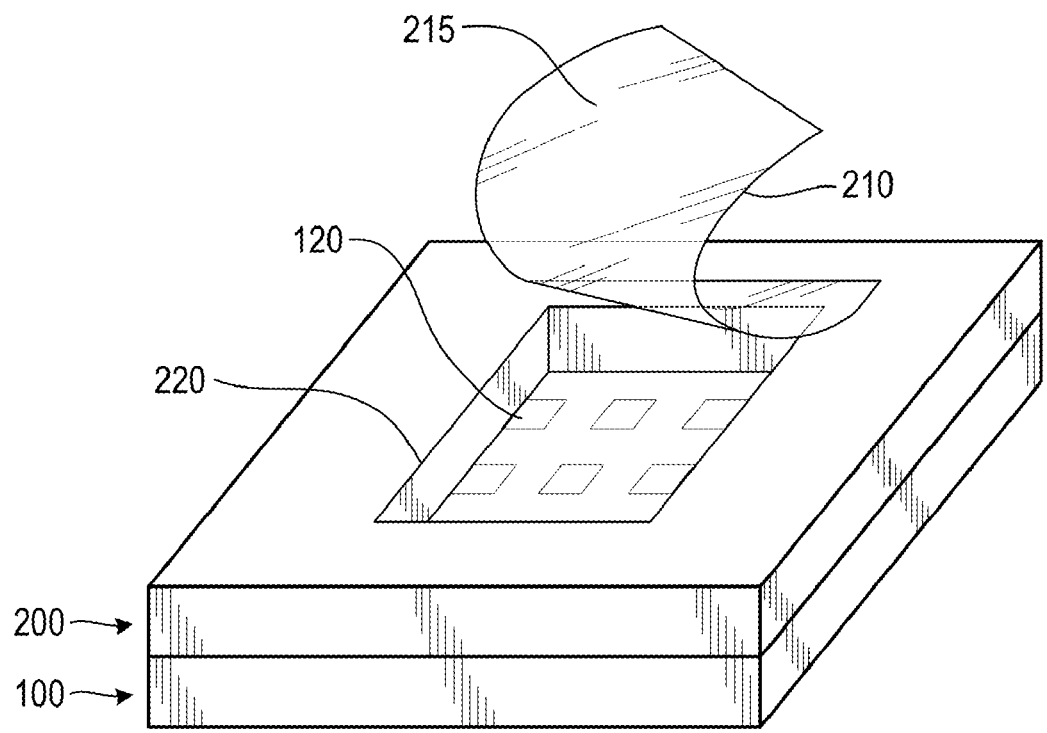
FIG. 1B is an assembled view of the packaged NERS-active structure of FIG. 1A.

A first embodiment of a packaged NERS-active structure 10 according to the invention is shown in FIGS. 1A and 1B.

FIG. 1A depicts the packaged NERS-active structure 10 in an exploded view, and FIG. 1B illustrates the packaged NERS-active structure 10 in assembled form. The packaged NERS-active structure 10 includes a NERS-active substrate 100 and a packaging substrate 200. The NERS-active substrate may comprise, by way of example, one of silicon, glass, quartz or plastic material. The NERS-active substrate 100 may include at least one NERS-active structure 120 on a first surface 110 thereof. FIG. 1A depicts a plurality of NERS-active structures 120 disposed on the first surface 110 in an array. Optionally, the plurality of NERS-active structures 120 may be randomly positioned. The at least one NERS-active structure 120 may be on a central region 130 of the substrate first surface 110. The NERS-active structures 120 may be formed of a NERS-active material, such as, for example gold, silver, copper, platinum, palladium, aluminum, or any other material that will enhance the Raman scattering of photons by analyte molecules positioned adjacent thereto.

The packaging substrate 200 may include an opening 220 therethrough, as depicted in FIG. 1B. The opening 220 may be sized to match the central region of the substrate first surface 110, enabling the NERS-active structures 120 to be accessed through the opening 220. A membrane 210 may cover the opening 220, as illustrated in FIG. 1A. The membrane 210 may be peeled back, as depicted in FIG. 1B, or otherwise removed to expose the NERS-active structures 120. The packaging substrate 200 may comprise one of silicon, glass, quartz, or plastic material.

One example of a suitable membrane 210 is a thin metal film. A current may be used to burn the metal film off to expose the NERS-active structures below. Thermally or optically degradable polymer films may also be used. Methods of removing a degradable polymer film include, by way of example and not limitation, laser ablation, microwave or acoustic decomposition, electrical, or thermal burn-off. A degradable polymer film covering the area of a NERS-site, which may be between about 1 $\mu m^2$ and about 100 $\mu m^2$ may be removed with a laser having a power of between about 2 and about 6 mW.

The membrane 210 may be reusable. A polymer film may be peeled back, for example, by using robotics, before an analyte is disposed on the substrate 100. The packaged NERS-active structure 10 may be used to perform NERS, as described below, then robotics may be used to replace the membrane 210, the sealing the NERS-active structure 120 and adjacent analyte (not shown) for archiving. The packaged NERS-active structure 10 may be stored, and the analyte may be tested again in the future.

A surface 215 of the membrane 210 (see FIG. 1B) may be passivated or coated with an inert substance such as fluorinated hydrocarbons. The coated surface 215 may be the surface facing the NERS-active structure 120, which protects the central region 130 of the substrate first surface 110 and the NERS-active structure 120 from unnecessary contamination.

The packaging substrate 200 may be secured to the substrate 100, for example, with a bonding material. One example of a suitable bonding material is a two-component reactive adhesive. Sealants and resins including acrylic, anaerobic materials, conductives, epoxy, polysulfides, polyurethanes, UV curable and other polymers may also be suitable. The packaging substrate 200 may be secured to the periphery of the substrate first surface 110, and the central region 130 may remain accessible through the opening 220 of the packaging substrate 200.

Figure 2:
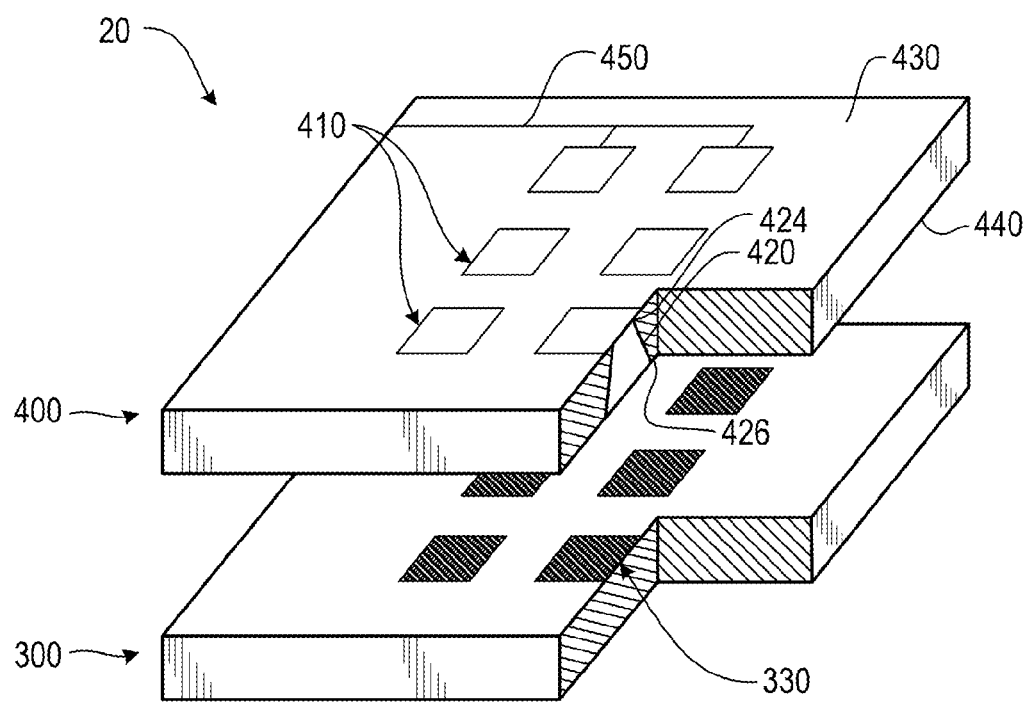
FIG. 2 is an exploded view of a second embodiment of a packaged NERS-active structure according to the invention.

FIG. 2 depicts a second embodiment of a packaged NERS substrate of the present invention. A NERS coupon 300 may be formed of a substrate made of, for example, silicon, glass, quartz, or plastic, with an array of NERS sites 330 thereon. The NERS coupon 300 may be between about 1 cm² to about 10 cm². Each NERS site 330 may be between about 1 μm² to about 200 μm². Anywhere from one to several millions of NERS sites 330 may be disposed on the NERS coupon 300. Each NERS site 330 comprises at least one NERS-active structure 120, as shown in FIG. 1A.

A packaging substrate 400 may include a plurality of openings 420 therein. Each opening 420 may be covered with a membrane 410. The packaging substrate may include a first surface 430 and an opposing, second surface 440. The second surface may be adjacent to the NERS coupon 300. The membranes 410 may be disposed on the first surface 430. Each opening 420 may optionally be tapered, with the area of the opening 424 at the first surface 430 being less than the area of the opening 426 at the second surface 440. The area of the membrane 410 may be greater than the area of the opening 424 at the first surface 430, enabling the membrane 410 to be adhered to, and supported by, the first surface 430 of the packaging substrate 400.

The openings 420 and associated membranes 410 may be formed using conventional microengineering techniques. For example, the packaging substrate 400 may be coated with a mask material on the first surface 430 and the second surface 440. The coating of the mask material on the second surface 440 may be patterned according to the desired locations of the openings 420. The packaging substrate 400 may be etched from the second surface 440 to form the openings 420. Each membrane 410 may be deposited in the desired location over the mask material on the first surface 430. For example, a negative photoresist may be used to define the desired locations of each membrane 410, and a layer comprising gold may be deposited by evaporation. The membranes 410 may be defined using a lift-off procedure, that is, by removing the resist and overlying portions of the gold layer in the undesirable locations, leaving the portions of the gold layer in the form of membranes 410.

Optionally, conductive traces 450 may be provided on the first surface 430 of the packaging substrate 400. The conductive traces 450 may be in electrical communication with each membrane 410 and may be used to burn off a conductive membrane, such as, for example, a metal film. Each membrane 410 may be removed selectively, with the other membranes 410 remaining intact. Alternatively, all of the membranes 410 may be removed simultaneously.

Thermally or optically degradable polymer films may also be used as the membranes 410. Methods of removing a degradable polymer film include, by way of example and not limitation, laser ablation, microwave or acoustic decomposition, electrical burn-off, or thermal burn-off. A degradable polymer film covering the area of a NERS-site, which may be between about 1 μm² and about 100 μm², may be removed with a laser having a power between about 2 and about 6 mW.

The membrane 410 may be reusable. A polymer film may be peeled back, for example, by using robotics, before an analyte is disposed on a NERS site 330 of the NERS coupon 300. The packaged NERS-active structure 20 may be used to perform NERS at one NERS site 330 as described hereinbelow, then robotics may be used to replace the membrane 410, sealing the NERS-active structure 120 and adjacent analyte (not shown) for archiving. The packaged NERS-active structure 20 may be stored, or other NERS sites 330 may be used for analyte testing. In this fashion, any analyte sealed within the packaged NERS-active structure 20 may be tested again in the future.

Figure 3:
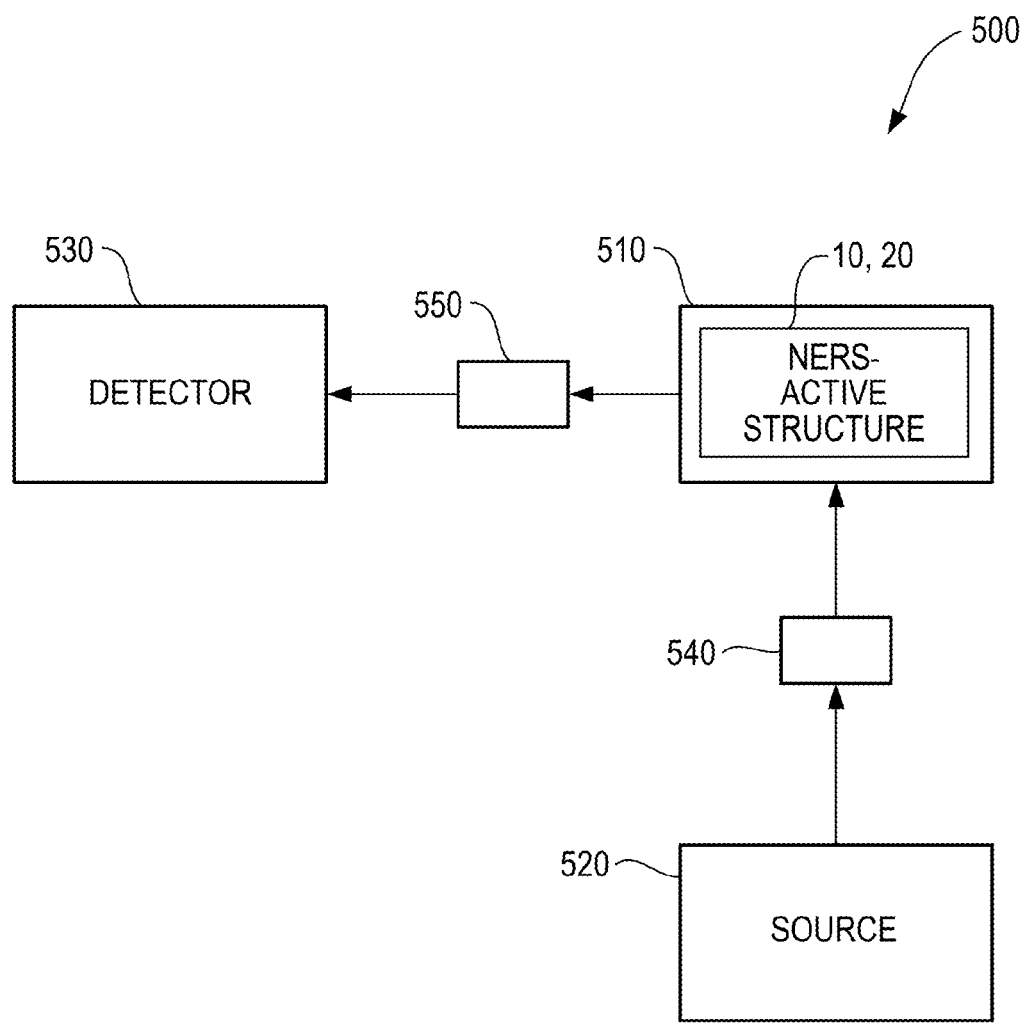
FIG. 3 is a schematic diagram of an exemplary system for performing nano-enhanced Raman spectroscopy using the packaged NERS-active structures of FIGS. 1A, 1B, and 2.

An exemplary NERS system 500 according to the invention is illustrated schematically in FIG. 3. The system 500 may include one of the exemplary packaged NERS-active structures 10, 20 and may be used to perform nano-enhanced Raman spectroscopy. The NERS system 500 may include a sample or analyte stage 510, an excitation radiation source 520, and a detector 530. The analyte stage 510 may include one of the packaged NERS-active structures 10, 20. The NERS system 500 also may include various optical components 540 positioned between the excitation radiation source 520 and the analyte stage 510, and various optical components 550 positioned between the analyte stage 510 and the detector 530.

The excitation radiation source 520 may include any suitable source for emitting radiation at the desired wavelength, and may be capable of emitting a tunable wavelength of radiation. For example, commercially available semiconductor lasers, helium-neon lasers, carbon dioxide lasers, light emitting diodes, incandescent lamps, and many other known radiation-emitting sources may be used as the excitation radiation source 520. The wavelengths that are emitted by the excitation radiation source 520 may include any suitable wavelength for properly analyzing the analyte using NERS. An exemplary range of wavelengths that may be emitted by the excitation radiation source 520 includes wavelengths between about 350 nm and about 1000 nm.

The excitation radiation emitted by the source 520 may be delivered either directly from the source 520 to the analyte stage 510 and the packaged NERS-active structure 10, 20. Alternatively, collimation, filtration, and subsequent focusing of the excitation radiation may be performed by optical components 540 before the excitation radiation impinges on the analyte stage 510 and the packaged NERS-active structure 10, 20.

The packaged NERS-active structure 10, 20 of the analyte stage 510 may enhance the Raman signal of the analyte, as previously discussed. In other words, irradiation of the NERS-active structure 10, 20 by excitation radiation may increase the number of photons inelastically scattered by an analyte molecule positioned near or adjacent to the packaged NERS-active structure 10, 20.

The Raman scattered photons may be collimated, filtered, or focused with optical components 550. For example, a filter or a plurality of filters may be employed, either as part of the structure of the detector 530 or as a separate unit that is configured to filter the wavelength of the excitation radiation, thus allowing only the Raman scattered photons to be received by the detector 530.

The detector 530 receives and detects the Raman scattered photons and may include a monochromator (or any other suitable device for determining the wavelength of the Raman scattered photons) and a device such as, for example, a photomultiplier for determining the quantity of Raman scattered photons (intensity).

Ideally, the Raman scattered photons are scaffered isotropically, being scattered in all directions relative to the analyte stage 510. Thus, the position of the detector 530 relative to the analyte stage 510 is not particularly important. However, the detector 530 may be positioned at, for example, an angle of 90° relative to the direction of the incident excitation radiation to minimize the intensity of the excitation radiation that may be incident on the detector 530.

To perform NERS using the system 500, a user may remove the membrane 210 and provide an analyte molecule or molecules adjacent to the NERS-active structure 120 of the packaged NERS-active structure 10, 20. The analyte and the NERS-active structure 120 are irradiated with excitation radiation or light from the source 520. Raman scattered photons scattered by the analyte are then detected by the detector 530. The membrane 210 may be replaced, or a new membrane 210 may be provided to replace the membrane 210, and preserve the analyte molecule or molecules within the packaged NERS-active structure.

The structures and systems disclosed herein may also be used to perform enhanced hyper-Raman spectroscopy. When excitation radiation impinges on an analyte molecule, a very small number of photons may be scattered at frequencies corresponding to the higher order harmonics of the excitation radiation, such as the second and third harmonics (i.e., twice or three times the frequency of the excitation radiation). Some of these photons may have a frequency that is Raman-shifted relative to the frequencies corresponding to the higher order harmonics of the excitation radiation. These higher order Raman-scattered photons can provide information about the analyte molecule that cannot be obtained by first order Raman spectroscopy. Hyper-Raman spectroscopy involves the collection and analysis of these higher order Raman-scattered photons.

Although the foregoing description contains many specifics, these are not to be construed as limiting the scope of the present invention, but merely as providing certain exemplary embodiments. Similarly, other embodiments of the invention may be devised which do not depart from the spirit or scope of the present invention. The scope of the invention is, therefore, indicated and limited only by the appended claims and their legal equivalents, rather than by the foregoing description. All additions, deletions, and modifications to the invention, as disclosed herein, which fall within the meaning and scope of the claims, are encompassed by the present invention.

What is claimed is:

1. A packaged NERS-active structure comprising:
   a substrate;
   at least one NERS-active structure disposed on the substrate;
   a packaging substrate having at least one opening therethrough disposed on the substrate, the opening being aligned with the at least one NERS-active structure;
   conductive traces provided on the packaging substrate; and
   a removable membrane covering the at least one opening, wherein the conductive traces are in electrical communication with the removable membrane, and wherein the removable membrane is to be burned off through application of an electrical current through the conductive traces.

2. The NERS-active structure of claim 1, further comprising a bonding material between the substrate and packaging substrate.

3. The NERS-active structure of claim 1, wherein the at least one NERS-active structure is usable for enhancing Raman scattered radiation in NERS.

4. The NERS-active structure of claim 1, wherein the at least one NERS-active structure comprises a NERS-active material.

5. The NERS-active structure of claim 1, wherein the substrate comprises plastic.

6. The NERS-active structure of claim 1, wherein the at least one NERS-active structure comprises a plurality of NERS sites, each NERS site comprising at least one NERS-active structure, and the packaging substrate includes a plurality of openings therethrough, each opening being aligned with a NERS site of the plurality of NERS sites.

7. The NERS-active structure of claim 1, wherein the removable membrane comprises gold.

8. The NERS-active structure of claim 1, wherein the removable membrane comprises a polymer film.

9. The NERS-active structure of claim 8, wherein the removable membrane comprises an optically or thermally degradable material.

10. The NERS-active structure of claim 6, further comprising a plurality of removable membranes, each removable membrane disposed over an opening of the plurality of openings, wherein the conductive traces are in electrical communication with the plurality of removable membranes, and wherein the plurality of removable membranes are to be selectively burned off through selective application of electrical current through the conductive traces.

11. A method of packaging a NERS active structure, comprising:
    providing at least one NERS active structure on a substrate;
    attaching a packaging substrate to the substrate, the packaging substrate having at least one opening therethrough, the at least one opening providing access to the at least one NERS active structure;
    providing at least one membrane covering the at least one opening in the packaging substrate; and
    providing a plurality of conductive traces on the packaging substrate in electrical communication with the at least one membrane, wherein the at least one membrane is to be burned off through application of an electrical current through the plurality of conductive traces.

12. The method of claim 11, further comprising a plurality of membranes and a plurality of openings, each membrane disposed over an opening of the plurality of openings, wherein the conductive traces are in electrical communication with the plurality membranes, and wherein the plurality of membranes are to be selectively burned off through selective application of the electrical current through the plurality of conductive traces.

13. A method of preserving an analyte on a NERS substrate for archiving, comprising:
    providing a packaged NERS-active structure comprising:
      a substrate;
      at least one NERS-active structure disposed on the substrate;
      a packaging substrate having at least one opening therethrough disposed on the substrate, the opening being aligned with the at least one NERS-active structure; and
      a membrane covering the opening;
      conductive traces provided on the packaging substrate in communication with the membrane;
    removing the membrane covering the opening through application of an electrical current through the conductive traces;
    placing an analyte molecule adjacent the at least one NERS-active structure; and
    covering the opening.

14. A method for forming a packaged NERS-active structure comprising:
    providing a substrate having a surface;
    affixing at least one NERS-active structure on the surface of the substrate;
    adhering a packaging substrate to the surface of the substrate, the packaging substrate having at least one opening therethrough, the at least one opening providing access to the at least one NERS-active structure;
    covering the at least one opening with at least one removable membrane; and
    providing a plurality of conductive traces on the packaging substrate in electrical communication with the at least one removable membrane, wherein the at least one membrane is to be burned off through application of an electrical current through the plurality of conductive traces.

15. The method of claim 14, wherein affixing at least one NERS-active structure on the surface of the substrate comprises affixing a plurality of NERS-active structures in the form of an array on the surface of the substrate.

16. The method of claim 14, wherein adhering a packaging substrate to the surface of the substrate comprises adhering a packaging substrate having a plurality of openings therethrough, wherein the openings are covered by a plurality of removable membranes, each opening providing access to at least one NERS-active structure of the plurality of NERS-active structures, wherein the plurality of conductive traces are in electrical communication with the plurality of removable membranes, and wherein the plurality of removable membranes are to be selectively burned off through selective application of the electrical current through the plurality of conductive traces.

* * * * *

UNITED STATES PATENT AND TRADEMARK OFFICE
CERTIFICATE OF CORRECTION

| | | |
|---|---|---|
| PATENT NO. | : 8,330,951 B2 | Page 1 of 1 |
| APPLICATION NO. | : 11/413516 | |
| DATED | : December 11, 2012 | |
| INVENTOR(S) | : Zhiyong Li et al. | |

It is certified that error appears in the above-identified patent and that said Letters Patent is hereby corrected as shown below:

In the Claims:

In column 8, line 31, in Claim 12, before "membranes," insert -- of --.

Signed and Sealed this
Fourteenth Day of May, 2013

Teresa Stanek Rea
*Acting Director of the United States Patent and Trademark Office*